US00PP16198P2

(12) United States Plant Patent
Swane

(10) Patent No.: US PP16,198 P2
(45) Date of Patent: Jan. 10, 2006

(54) FLORIBUNDA ROSE PLANT NAME 'PROSE'

(50) Latin Name: *Rosa hybrida*
Varietal Denomination: PROse

(75) Inventor: Edgar Norman Swane, Dural (AU)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 70 days.

(21) Appl. No.: 10/856,188

(22) Filed: May 28, 2004

(51) Int. Cl.
*A01H 5/00* (2006.01)

(52) U.S. Cl. ..... Plt./149
(58) Field of Classification Search ..... Plt./149
See application file for complete search history.

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety of Floribunda rose suitable for garden decoration, having flowers of deep purple coloration with lighter reverse.

1 Drawing Sheet

Classification: The present invention relates to a new *Rosa hybrida* plant.

Variety denomination: The new plant has the varietal denomination 'PROse'.

BACKGROUND OF THE INVENTION

This invention relates to a new and distinct variety of Floribunda Rose. It was discovered in the autumn of 1998 in Dural, New South Wales, Australia as a mutation of the cultivar 'PRObril' (U.S. Plant Pat. No. 12,645). It was discovered by Edgar Norman Swane, Galston Road, Dural, New South Wales, Australia.

SUMMARY OF THE INVENTION

Among the features that distinguish the new variety from other presently available and known commercial rose cultivars are the following combination of characteristics: its deep purple colored flowers with lighter reverse, its prolific bloom and its dark burgundy red stamens and anthers. The plant is a bushy rounded growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'PROse' may be asexually propagated by cuttings, budding or grafting. The budding and grafting successfully occurred on the plant/rootstock *Rosa hybrida* cv. 'Dr. Huey'.

COMPARISON WITH PARENTS

The new rose may be distinguished from its parent, 'PRObril', by the following combination of characteristics: whereas 'PRObril' bears flowers of deep pink and cream coloration, 'PROse' bears flowers of deep purple coloration with a lighter reverse. 'PRObril' bears flowers with dark pink stamens and anthers, whereas 'PROse' bears flowers with significantly darker burgundy red stamens and anthers.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of 3 to 4 year-old rose plants of the new variety grown outdoors in Upland, Calif. in the month of May. Phenotypic expression may vary with environmental, cultural and climatic conditions, as well as differences in conditions of light and soil.

FLOWER

The new variety sometimes bears its flowers singly, usually in clusters of three to four or more per stem. Flowers are borne in regular somewhat rounded clusters on medium length stems (about 20 to about 35 cm.). Outdoors, the plant blooms very abundantly and nearly continuously during the growing season. The flowers have a very slight fragrance.

BUD

The peduncle is about 3.0 to about 5.9 cm. in length, of somewhat slender caliper, and usually erect. It is moderately smooth with numerous stipitate glands. Peduncle color is between 144A and 138B, sometimes lightly suffused, especially on the side exposed to the sun, with between 182A and 184C.

Before the calyx breaks, the bud is about 1.1 to about 1.7 cm. in diameter at the widest point, about 1.8 to about 2.5 cm. in length, and very pointed to somewhat ovoid in shape. The surface of the bud bears some stipitate glands usually with slender foliaceous parts extending beyond the tip of the bud about ¼ or more of its length. Bud color is between 144A and 137C sometimes lightly suffused, especially on the side exposed to the sun, with between 182A and 184C.

The sepals are about 1.5 to about 2.1 cm. in length and about 0.6 to about 0.8 cm. in width at the widest point. The outer surface color of the sepal is between 144A and 137C sometimes lightly suffused, especially on the side exposed to the sun, with between 182A and 184C. The inner surface color of the sepal is between 138B and 147C and covered with fine wooly tomentum; sepal margins are lined with many stipitate glands and hairs.

As the petals open (after the calyx breaks), the bud is about 1.4 to about 2.1 cm. in diameter at the widest point, about 1.9 to about 2.6 cm. in length, and very pointed to somewhat ovoid in form. The color of the under surfaces of the newly opened petals is between 155C and 155A usually heavily blushed with between 64A and 71A. At the point where the petal attaches, there is a very small zone of between 4D and 2D. The color of the upper surfaces of the newly opened petals is between 71B and 71C at the base of the petal that gradually suffuses near the center of the petal to as dark as between 187A and 60B. At the point where the petal attaches, there is a somewhat large zone of between 2D and 4D.

BLOOM

When fully open, the bloom ranges from about 8.1 to about 10.9 cm. in diameter. Petalage is double with about 27 to 32 petals and about 1 to 3 petaloids arranged irregularly. When partially open, the bloom form is moderately globular to somewhat cupped and the petals are somewhat loosely spiraled to cupped with petal edges slightly reflexed outward. When fully open, the bloom form is moderately cupped to somewhat flat, and the petals are somewhat cupped to slightly undulated with petal edges moderately reflexed outward and sometimes slightly rolled mostly on the inside petals.

PETALS

The substance of the petals is somewhat thin with upper surfaces moderately satiny to somewhat velvety and under surfaces lightly shiny to matte. The outer petals are nearly round to broadly obovate in shape with rounded apices. The inner petals are more narrowly obovate in shape with rounded apices. The petals are about 2.9 to about 4.3 cm. in length and about 1.7 to about 3.4 cm. in width at the widest point. Petal margins are entire.

NEWLY OPENED FLOWER

The under surface of the outer, intermediate and inner petals is between 155A and 155C usually lightly blushed with between 71C and 72A. There is no visible change in coloration at the point where the petal attaches.

The upper surface of the outer, intermediate and inner petals is between 67A and 71C at the base of the petal that gradually suffuses near the center of the petal to darker then between 71A and 61A. At the point where the petal attaches, there is a somewhat small zone of near 155A.

The general tonality of the newly opened flower is between 67A and 71C at the base of the petal that gradually suffuses near the center of the petal to darker then between 71A and 61A.

THREE-DAY-OLD FLOWER

The under surface of the outer and inner petals is between 155B and 155D usually lightly blushed with between 71C and 72A. There is no visible change in coloration at the point where the petal attaches.

The upper surface of the outer and inner petals is between 67A and 71C at the base of the petal that gradually suffuses near the center of the petal to darker then between 71A and 61A. At the point where the petal attaches, there is a somewhat small zone of between 155B and 155D.

The general tonality of the three-day-old flower is between 67A and 71C at the base of the petal that gradually suffuses near the center of the petal to darker then between 71A and 61A.

On the spent bloom, the petals usually drop off cleanly.

In May in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (approximately 85) and are arranged regularly about the pistils; a few are mixed with petaloids. The filaments are of medium length (about 0.4 to about 0.9 cm.), most with anthers. Filaments are between 59A and 187A in color. The anthers are moderately small for the class and all open approximately at the same time. Anther color is between 187A and 11D when immature and between 200B and 202A at maturity.

FEMALE REPRODUCTIVE ORGANS

Pistils vary in number (approximately 35). The styles are moderately even, average in length (0.3 to about 0.6 cm.), somewhat thin in caliper, and moderately bunched. Stigma color is between 4D and 8D. Style color is between 53C and 60A. Ovaries are usually all enclosed in the calyx.

Hips are average in length (about 2.1 to about 2.7 cm.), somewhat obovate to ovoid in form, and near 33B in color when ripe. The hip surface is very smooth with thick fleshy walls. The sepals are fugacious and usually straight in shape. The seeds are irregularly rounded, smooth in texture, approximately 6 to about 14 per hip, about 0.4 to about 0.7 cm. in diameter at the widest point and between 160C and 162C in color.

FOLIAGE

The compound leaves are usually comprised of three to five or more leaflets and are borne abundantly. The five-leaflet leaves are about 9.9 to about 19.1 cm. in length and about 8.7 to about 15.8 cm. in width at the widest point, moderately leathery to somewhat crisp in texture, and semi-glossy in finish. The terminal leaflets are about 5.8 to about 9.3 cm. in length and about 2.9 to about 5.5 cm. in width at the widest point, shaped moderately ovate to somewhat oblong with acute apices and rounded to somewhat acute bases. Their margins are simply serrate.

The upper surface color of the mature leaf is between 147A and 137B. The under surface color of the mature leaf is between 147C and 136C. The upper surface color of the young leaf is between 144A and 137C, sometimes lightly suffused with near 183C. The under surface color of the young leaf is between 138B and 136C, sometimes lightly suffused with near 183D.

The rachis is somewhat light to average in caliper and moderately rough. The upper side is shallowly grooved with very few stipitate glands and hairs on the edges of the grooves. The under side of the rachis is moderately rough with few small prickles and some hairs. The rachis color is between 144A and 146B sometimes lightly suffused, especially on the young leaves with near 183C.

The stipules are about 1.4 to about 1.8 cm. in length and of medium width (about 0.4 to about 0.6 cm.) with moderately long straight points that usually turn out at an angle of more than 45 degrees. The stipules color is between 144A and 146B sometimes lightly suffused, especially on the young leaves near 183C.

The petiole is about 0.7 to about 1.6 cm. in length and about 0.2 to about 0.3 cm in diameter at the widest point. The petiole color is between 144A and 146B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy rounded medium height growth habit (about 75 to about 90 cm. in height and about 80 to about 100 cm. spread at the widest point), with very full branching. It displays very vigorous growth and the canes are of somewhat light caliper.

The color of the major stems is between 144B and 148A. They bear very few medium sized and small prickles that are about 0.3 to about 0.6 cm. in length. The prickles are almost straight angled slightly downward with a somewhat short to medium length moderately broad to nearly round base; prickle color is between 164A and 166B.

The color of the branches is between 144A and 137B. They bear very few medium sized and small prickles which are of similar size and shape to the prickles on the major stems; prickle color is between 160B and 162C.

The color of the new shoots is between 144A and 137B often moderately suffused with between 183D and 181C. They bear very few medium sized and small prickles which are of similar size and shape to the prickles on the major stems; prickle color is near 162D often moderately suffused with between 183D and 181C.

I claim:

1. A new and distinct Floribunda rose plant of the variety substantially as described and illustrated herein.

* * * * *

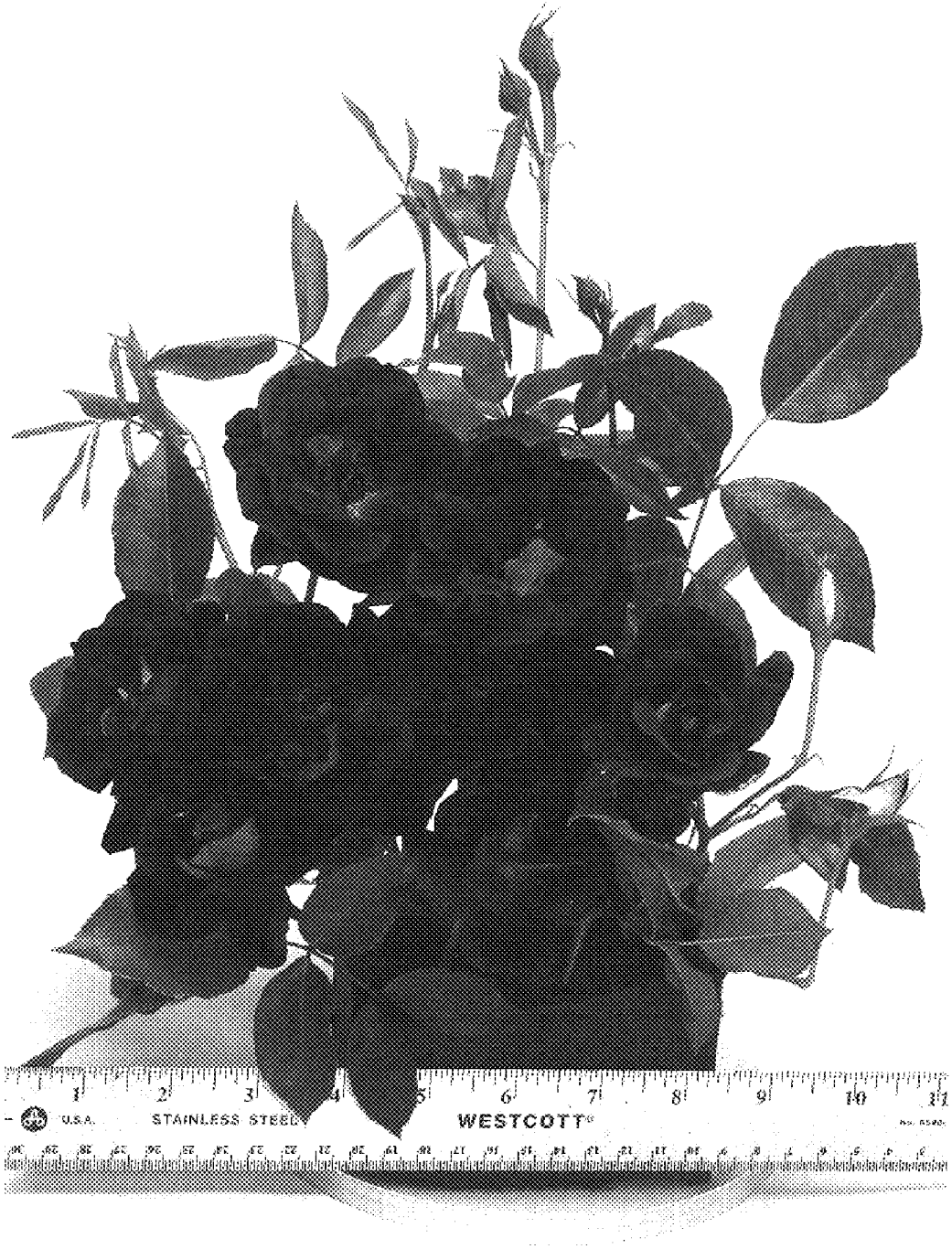
U.S.A.
STAINLESS STEEL
WESTCOTT